United States Patent [19]

Hackenberger et al.

[11] Patent Number: 4,927,935
[45] Date of Patent: May 22, 1990

[54] 3-CYANOQUINOLINE DERIVATIVES

[75] Inventors: Alfred Hackenberger, Paulo; Manfred Patsch, Wachenheim, both of Fed. Rep. of Germany

[73] Assignee: BASF Aktiengesellschaft, Ludwigshafen, Fed. Rep. of Germany

[21] Appl. No.: 268,264

[22] Filed: Nov. 7, 1988

Related U.S. Application Data

[63] Continuation-in-part of Ser. No. 60,165, Jun. 10, 1987, abandoned.

[30] Foreign Application Priority Data

Jun. 21, 1986 [DE] Fed. Rep. of Germany ....... 3620856

[51] Int. Cl.$^5$ .......................................... C07D 215/54
[52] U.S. Cl. .................... 546/157; 546/153; 546/168; 546/169; 546/170; 546/171; 546/172; 546/176; 546/177
[58] Field of Search ............... 546/153, 157, 168, 171, 546/180, 152, 172, 176, 177, 169, 170

[56] References Cited

U.S. PATENT DOCUMENTS

| | | | |
|---|---|---|---|
| 4,220,779 | 9/1980 | Ehrig et al. | 546/152 |
| 4,339,431 | 7/1982 | Gaffar. | |
| 4,534,881 | 8/1985 | Sikes et al. | |

FOREIGN PATENT DOCUMENTS

| | | |
|---|---|---|
| 8203008 | 9/1982 | Australia. |
| 2206506 | 8/1973 | Fed. Rep. of Germany. |
| 2307444 | 8/1974 | Fed. Rep. of Germany. |
| 3620856 | 12/1987 | Fed. Rep. of Germany. |

Primary Examiner—Anton H. Sutto
Assistant Examiner—E. Bernhardt
Attorney, Agent, or Firm—Oblon, Spivak, McClelland, Maier & Neustadt

[57] ABSTRACT

A compound of the formula I

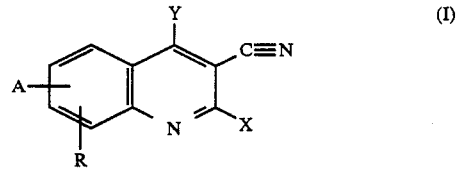

where A is nitro, amino, halocarbonyl or halosulfonyl, R is hydrogen, halogen, nitro, cyano, $C_1$-$C_4$-alkanoylamino, hydroxyl, $C_1$-$C_4$-alkoxy phenoxy which is unsubstituted by methyl or chloro, mercapto, $C_1$-$C_4$-alkylthio, phenylthio which is unsubstituted or substituted by ethyl, fluoro, or methoxy, carboxyl, $C_1$-$C_4$-alkoxycarbonyl, phenoxycarbonyl which is unsubstituted or substituted by isopropyl, bromo, or methoxy, carbamoyl, hydroxysulfonyl, $C_1$-$C_4$-alkylsulfonyl, phenylsulfonyl which is unsubstituted or substituted by ethyl, chloro, or isopropoxy, sulfamoyl or trifluoromethyl or is $C_1$-$C_4$-alkyl which may be substituted by hydroxyl, $C_1$-$C_4$-alkoxy or halogen, and X and Y are each, independently of one another, halogen, hydroxysulfonyl, $C_1$-$C_4$-alkoxy or phenoxy which is unsubstituted or substituted by methyl or chloro, phenoxy, subject to the proviso that at least one of X and Y is halogen.

3 Claims, No Drawings

3-CYANOQUINOLINE DERIVATIVES

This application is a continuation-in-part of U.S. Ser. No. 07/060,165, filed June 10, 1987 now abandoned.

BACKGROUND OF THE INVENTION

1. Field of the Invention

The present invention relates to compounds of the formula I

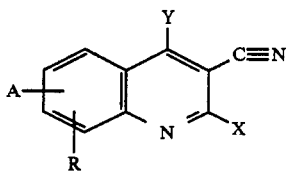

where
- A is nitro, amino, halocarbonyl or halosulfonyl,
- R is hydrogen, halogen, nitro, cyano, $C_1$-$C_4$-alkanoylamino, hydroxyl, $C_1$-$C_4$-alkoxy, substituted or unsubstituted phenoxy, mercapto, $C_1$-$C_4$-alkylthio, substituted or unsubstituted phenylthio, carboxyl, $C_1$-$C_4$-alkoxycarbonyl, substituted or unsubstituted phenoxycarbonyl, carbamoyl, hydroxysulfonyl, $C_1$-$C_4$-alkylsulfonyl, substituted or unsubstituted phenylsulfonyl, sulfamoyl or trifluoromethyl or is $C_1$-$C_4$-alkyl which may be substituted by hydroxyl, $C_1$-$C_4$-alkoxy or halogen, and
- X and Y are each, independently of one another, halogen, hydroxysulfonyl, $C_1$-$C_4$-alkoxy or substituted or unsubstituted phenoxy, subject to the proviso that at least one of X and Y is halogen.

Where the 3-cyanoquinoline derivatives of the formula I have one or more hydroxysulfonyl radicals and/or a carboxyl radical, the definition is also to cover the salts thereof, in particular the alkali metal salts, e.g., the sodium or potassium salts.

Where the phenyl radicals which appear in the formula I are substituted, suitable substituents are $C_1$-$C_4$-alkyl, halogen, in particular fluorine, chlorine or bromine, or $C_1$-$C_4$-alkoxy.

R, X and Y in the formula I are, for example, fluorine, chlorine, bromine, methoxy, ethoxy, propoxy, isopropoxy, butoxy, isobutoxy, sec-butoxy, phenoxy, 4-methylphenoxy, 2-chlorophenoxy, or 2,4-dichlorophenoxy.

R in the formula I can also be for example formylamino, acetylamino, propionylamino, butyrylamino, isobutyrylamino, methylthio, ethylthio, propylthio, isopropylthio, butylthio, isobutylthio, sec-butylthio, phenylthio, 2-ethylphenylthio, 4-fluorophenylthio, 4-methoxyphenylthio, methoxycarbonyl, ethoxycarbonyl, propoxycarbonyl, butoxycarbonyl, sec-butoxycarbonyl, phenoxycarbonyl, 4-isopropylphenoxycarbonyl, 2-bromophenoxycarbonyl, 4-methoxyphenoxycarbonyl, methylsulfonyl, ethylsulfonyl, propylsulfonyl, butylsulfonyl, 2-ethylphenylsulfonyl, 2,4-dichlorophenylsulfonyl, 4-isopropoxyphenylsulfonyl, methyl, ethyl, propyl, isopropyl, butyl, isobutyl, secbutyl, 2-chloroethyl, 2-hydroxyethyl, 2-methoxyethyl, 2-ethoxyethyl or 2- or 3-hydroxypropyl.

Preference is given to cyanoquinolines of the formula I where X and Y are each fluorine or where one of X and Y is fluorine or chlorine and the other is hydroxysulfonyl.

Particular importance is given to compounds of the formula II

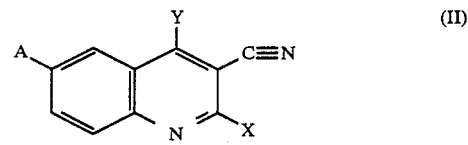

where A is nitro or amino, and X and Y are each fluorine, chlorine or hydroxysulfonyl.

To prepare the compounds according to the invention, it is possible for example to react an isatoic anhydride of the formula III

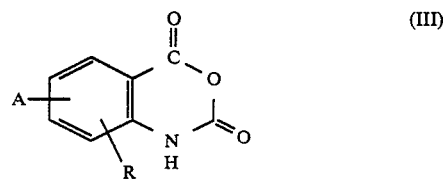

where A and R each have the above-mentioned meanings, with an alkyl cyanoacetate. The resulting 3-cyano-2,4-dihydroxyquinoline derivative can then be converted in a conventional manner, for example by reaction with phosphorus oxychloride, into the corresponding 2,4-dichloro compound.

The dichloro compound can then be converted with a metal fluoride, for example sodium fluoride or potassium fluoride, or with hydrogen fluoride into the corresponding 2,4-dichloro compound.

The dichloro and difluoro compounds can be subjected to a nucleophilic substitution reaction, for example with the sulfite anion or with a hydroxy compound such as methanol, ethanol or phenol, to give a compound according to the invention where a halogen atom has been replaced.

The introduction of some of the substituents A and R can also be carried out directly on 3-cyano-2,4-dihydroxyquinoline by electrophilic substitution. Examples are nitration and sulfonation.

The compounds according to the invention are suitable for use as the fiber-bonding sites of reactive dyes, as intermediates for active substances and, where A is amino, even as diazo components.

As fiber-bonding sites the quinoline compounds react with the hydroxyl groups of e.g. cellulose. In this reaction the radical X and/or Y which is halogen is replaced by an oxygen atom of a cellulose hydroxyl group. When both radicals X and Y are halogen both of them may be replaced.

The linkage between dye and fiber-bonding site is according to the following scheme:

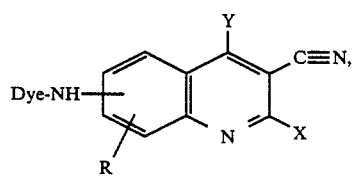

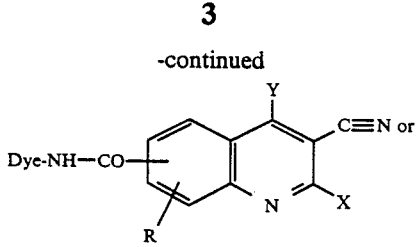

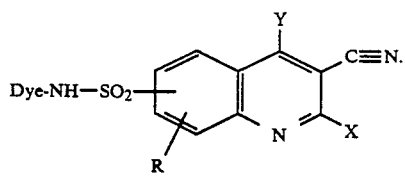

When the radical A is amino the 3-cyanoquinoline derivatives are also suitable as diazo components, which after diazotization and coupling with a coupling component KH give dyes of the formula

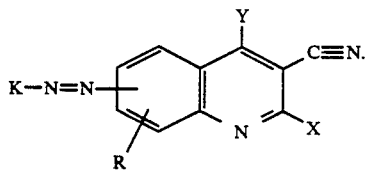

In principle, practically any desired chromophoric system can be combined with reactive groups to produce reactive dyes. Commonly used chromogens include azo, metallized azo, anthraquinone, phthalocyanine, and metal-complex formazan derivatives. Azo compounds comprise the widest range of shade from greenish-yellow to black. For yellow dyes, coupling products of pyrazolones and amino pyrazoles are commonly used. Pyridone derivatives have gained importance recently as coupling components for yellow dyes. Brilliant red colors are used based on aminohydroxynaphthalene disulfonic acids. Chromium, copper and cobalt metal-complex azo dyes made up the majority of metallized azo dyes. These dyes possess excellent light fastness. Brilliant blue and green reactive dyes with high fastness to light are the main contribution of anthraquinone derivatives. Copper and nickel phthalocyanine reactive dyes give bright turquoise shades and good wash fastness and satisfactory crocking fastness. Bright blue to green metal complex dyes from formazan derivatives are described in British Patent Nos. 1,191,741 and 1,219,383.

Additional information on the nature of the chromophoric group (the dye), the fiber, and the types of reactions involved in connecting the dye to the fiber via the bridging group is provided in *Kirk-Othmer's Encyclopedia of Chemical Technology*, Volume 8, "Reactive Dyes", 1979.

The examples which follow serve to illustrate the invention in more detail. The parts and percentages are by weight, unless otherwise stated.

EXAMPLE 1

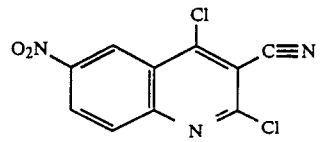

3-Cyano-2,4-dihydroxy-6-nitroquinoline 93 parts of 3-cyano-2,4-dihydroxyquinoline were dissolved in 990 parts of concentrated sulfuric acid. A mixture of 212 parts of concentrated sulfuric acid in 161 parts of 65% strength nitric acid was added dropwise at 0°–10° C. This was followed by 2 hours of stirring, precipitation onto ice, removal of the precipitated nitroquinoline by filtration, with suction and washing with water until acid-free. Drying gave 102 parts of crude product (corresponding to a yield of 88.3%).

3-Cyano-2,4-dichloro-6-nitroquinoline 231 parts of 3-cyano-2,4-dihydroxy-6-nitroquinoline were introduced into 770 parts of phosphorus oxychloride. 109 parts of triethylamine were then added dropwise in such a way that the temperature rose to 80° C. After an hour of stirring, a further 231 parts of 3-cyano-2,4-dihydroxy-6-nitroquinoline were added, followed by a further 109 parts of triethylamine. The temperature was then gradually raised to 140° C. After stirring at that temperature for 2 hours the mixture was cooled down and poured onto ice-water, and the precipitate was filtered off with suction and washed with water until acid-free. Drying gave 505 parts of crude 3-cyano-2,4-dichloro-6-nitroquinoline (corresponding to a yield of 94%). After recrystallization from ethyl acetate, the sample had a melting point of 190°–192° C.

EXAMPLE 2

3-Cyano-2,4-difluoro-6-nitroquinoline

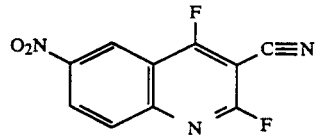

107 parts of 3-cyano-2,4-dichloro-6-nitroquinoline and 69 parts of KF were suspended in 520 parts of toluene. The toluene was distilled off, and 480 parts of N,N-dimethylformamide were added. The mixture was stirred at 90° C. for 3 hours, cooled down and poured onto ice-water, and the precipitated product was filtered off with suction and washed with water until salt-free. Drying gave 90 parts of 3-cyano-2,4-difluoro-6-nitroquinoline (corresponding to a yield of 96%). After recrystallization from ethyl acetate, a sample had a melting point of 128°–129° C.

EXAMPLE 3

6-Amino-3-cyano-2,4-difluoroquinoline

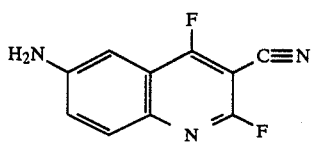

130 parts of anhydrous sodium sulfate were suspended in a solution of 305 parts of 3-cyano-2,4-difluoro-6-nitro-quinoline in 3,400 parts of tetrahydrofuran. 30 parts of a hydrogenation catalyst (10% palladium on carbon) were added, which was followed by hydrogenation at 40° C. and 3 bar. After the uptake of hydrogen had ended, the suspension was filtered, and the clear solution was added to 6,000 parts of ice-water. The resulting precipitate was filtered off with suction, washed and dried. This gave 198 parts of 6-amino-3-cyano-2,4-difluoroquinoline, corresponding to a yield of 74%.

The product has a melting point of 199°–202° (decomposition with escape of gas).

EXAMPLE 4

6-Amino-3-cyano-2,4-dichloroquinoline

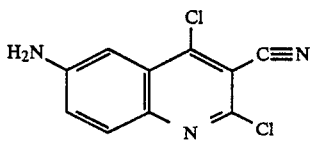

The compound was obtained by reducing 3-cyano-2,4-dichloro-6-nitroquinoline as described in Example 3. UV (THF): $\lambda_{max}/\epsilon = 415.2$ (3,189), 304.6 (7,675), 274.0 (43,425).

EXAMPLE 5

Reaction of 6-amino-3-cyano-2,4-difluoroquinoline with sodium sulfite

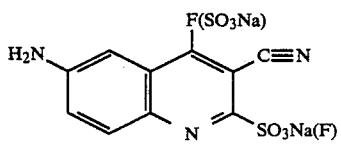

79 parts of anhydrous sodium sulfite were dissolved in 500 parts of water. 82 parts of 6-amino-3-cyano-2,4-difluoroquinoline were added and stirred in for 3 hours. After cooling down to 10° C., the precipitated product was filtered off with suction and washed with a little water. Drying gave 112 g of a uniform product in which a fluorine atom had been replaced by a sulfonic acid group, the sulfonic acid being obtained in the form of the sodium salt with one molecule of water of crystallization. The yield was 90%.

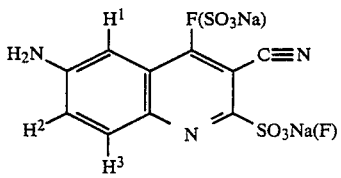

$^1$H-NMR (d$_6$.DMSO): $\delta = 8.02$ (d, 1H, H$^1$); 7.80–7.31 (s,s,d,d,2H,AB system H$^2$H$^3$; $J_{AB}=9$ Hz), 5.95 (s,2H,NH$_2$), 3.43 (s,2H,H$_2$O); UV (H$_2$O): $\lambda_{max}/\epsilon = 407.7$ (3,057), 265 (27,744), the $\epsilon$ being based on the anhydrous Na salt.

EXAMPLE 6

Reaction of 6-amino-3-cyano-2,4-dichloroquinoline with sodium sulfite

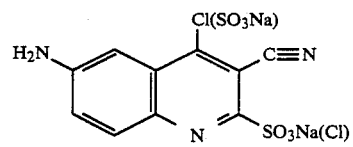

118 parts of anhydrous sodium sulfite were dissolved in 500 parts of water. 95 parts of 6-amino-3-cyano-2,4-dichloroquinoline were added, the mixture was subsequently stirred at 80° C. for 3 hours and then cooled down to 10° C., and the precipitated product was filtered off with suction and washed with a little water. Drying gave 83 g of a uniform product in which a chlorine atom had been replaced by a sulfonic group, the sulfonic acid being obtained in the form of the sodium salt with one molecule of water of crystallization.

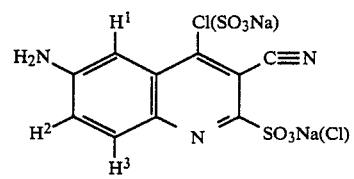

$^1$HNMR (d$_6$.DMSO): $\delta = 8.02$ (d,1H,H$^1$); 7.85–7.30 (s,s,d,d,2H,AB system H$^2$H$^3$; $J_{AB}=9$ Hz), 6.10 (s,2H,NH$_2$), 3.40 (s,2H,H$_2$O); UV (H$_2$O): $\lambda_{max}/\epsilon = 417.2$ (2,978), 275 (321,111), the $\epsilon$ being based on the anhydrous Na salt.

EXAMPLE 7

Reaction of 3-cyano-2,4-difluoro-6-nitroquinoline with ethanol

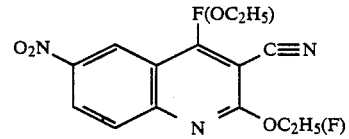

188 parts of 3-cyano-2,4-difluoro-6-nitroquinoline were dissolved in 1,200 parts of absolute ethanol. 51 parts of sodium carbonate were suspended in the solution and refluxed for two hours. The mixture was then filtered hot, the filtrate was cooled down to 0°–5° C. and the resulting crystals were filtered off with suction.

EXAMPLE 8

The reaction of 3-cyano-2,4-dichloro-6-nitroquinoline with ethanol as described in Example 7 produced a compound of the following formula (melting point 176°–178° C.).

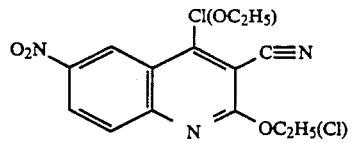

EXAMPLE 9

Catalytic reduction of the product obtained in Example 7 in tetrahydrofuran (catalyst Pd/C, 10%) gave an amine of the following formula (decomposition point 178° C.).

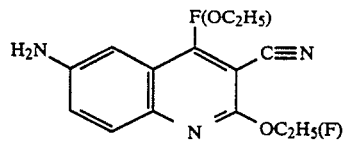

EXAMPLE 10

6-Chlorosulfonyl-3-cyano-2,4-dichloroquinoline

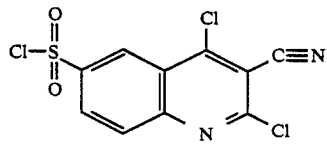

(a) 3-Cyano-2,4-dihydroxy-6-hydroxysulfonylquinoline 280 parts of 3-cyano-2,4-dihydroxyquinoline were introduced into 1,000 parts of chlorosulfonic acid. This was followed by stirring at 80° C. for 5 hours, cooling down, pouring onto ice-water, filtering off with suction and washing with water. The crude product obtained after drying need not be purified for chlorination.

(b) 6-Chlorosulfonyl-3-cyano-2,4-dichloroquinoline

The product obtained under (a) was chlorinated as described in Example 1 to give 6-chlorosulfonyl-3-cyano-2,4-dichloroquinoline which, after recrystallization from ethyl acetate, had a melting point of 168°–171° C.

What is claimed as new and desired to be secured by Letters Patent of the United States is:

1. A compound of the formula I

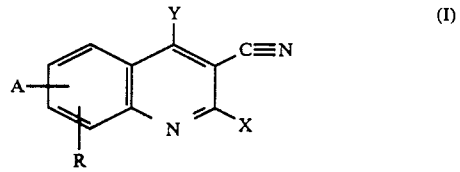

where

A is nitro, amino, halocarbonyl or halosulfonyl,

R is hydrogen, halogen, nitro, cyano, $C_1$–$C_4$-alkanoyl-amino, hydroxyl, $C_1$–$C_4$-alkoxy, phenoxy which is unsubstituted or substituted by methyl or chloro, mercapto, $C_1$–$C_4$-alkylthio, phenylthio which is unsubstituted or substituted by ethyl, fluoro, or methoxy, carboxyl, $C_1$–$C_4$-alkoxycarbonyl, phenoxycarbonyl which is unsubstituted or substituted by isopropyl, bromo, or methoxy, carbamoyl, hydroxysulfonyl, $C_1$–$C_4$-alkylsulfonyl, phenylsulfonyl which is unsubstituted or substituted by ethyl, chloro, or isopropoxy, sulfamoyl or trifluoromethyl or is $C_1$–$C_4$-alkyl which is unsubstituted or substituted by hydroxyl, $C_1$–$C_4$-alkoxy or halogen, and X and Y are each, independently of one another, halogen, hydroxysulfonyl, $C_1$–$C_4$-alkoxy or phenoxy which is unsubstituted or substituted by methyl or chloro, or phenoxy, subject to the proviso that at least one of X and Y is halogen.

2. The compound as claimed in claim 1, of the formula II

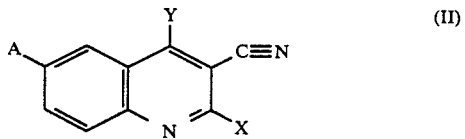

where

A is nitro or amino and X and Y are each independently of one another fluorine, chlorine or hydroxysulfonyl.

3. The compound as claimed in claim 1, wherein X and Y are each fluorine, or wherein one of X and Y is fluorine or chlorine and the other is hydroxysulfonyl.

* * * * *